United States Patent [19]

Zeidler et al.

[11] 4,376,120

[45] Mar. 8, 1983

[54] THERAPEUTIC COMPOSITIONS WITH A CYTOSTATIC ACTION CONTAINING ISOCYANURIC ACID DERIVATIVES AND PROCESS OF MANUFACTURE

[75] Inventors: Ulrich Zeidler; Herbert Fischer, both of Dusseldorf; Brigitte Hase, Erkrath; Hinrich Möller, Monheim; Hans-Christoph Wilk, Neuss, all of Fed. Rep. of Germany

[73] Assignee: Henkel Kommanditgesellschaft Auf Aktien, Dusseldorf-Holthausen, Fed. Rep. of Germany

[21] Appl. No.: 289,392

[22] Filed: Aug. 3, 1981

[30] Foreign Application Priority Data

Aug. 14, 1980 [AT] Austria .................. A 4169/80

[51] Int. Cl.³ .................. C07D 251/34; A61K 31/53
[52] U.S. Cl. .................. 424/249; 544/221
[58] Field of Search .................. 544/221; 424/249

[56] References Cited

U.S. PATENT DOCUMENTS

| | | | |
|---|---|---|---|
| 3,770,731 | 11/1973 | Jaeger | 544/221 |
| 3,779,949 | 12/1973 | Porret et al. | 544/221 |
| 3,910,908 | 10/1975 | Price | 544/221 |
| 3,914,225 | 10/1975 | Hiestand et al. | 544/221 |
| 3,920,689 | 11/1975 | Jaeger | 544/221 |

OTHER PUBLICATIONS

Kamata., Chemical Abstracts, vol. 90, entry 187948 (1979).

*Primary Examiner*—John M. Ford
*Attorney, Agent, or Firm*—Hammond & Littell, Weissenberger and Muserlian

[57] ABSTRACT

New cytostatic compounds based on isocyanuric acid derivatives having 2 or 3 epoxide group containing substituents on ring nitrogen atoms, of which at least one differs from a glycidyl, having the formula

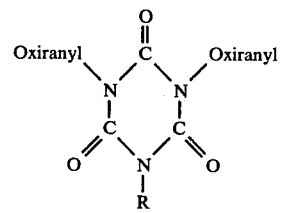

wherein Oxiranyl is the same or different and has the formula

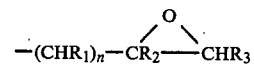

wherein $R_1$, $R_2$ and $R_3$ are the same or different and members selected from the group consisting of hydrogen, alkyl, haloalkyl, hydroxyalkyl and alkoxyalkyl and n in an integer from 1 to 8, with the proviso that if n is 1 in all oxiranyl groups, at least one of $R_1$ or $R_3$ is other than hydrogen, and R is a member selected from the group consisting of oxiranyl as defined above, hydrogen, alkyl, alkenyl, hydrocarbon aryl, hydrocarbon aralkyl, hydrocarbon alkaryl, cycloalkyl, and cycloalkenyl, optionally containing substituents.

When $R_1$, $R_2$ and/or $R_3$ denote alkyl or substituted alkyl in the oxiranyl radical, the alkyl radicals preferably have from 1 to 4 carbon atoms. The total number of carbon atoms in one oxiranyl radical should not be more than 10. The preparation of these compounds by introducing oxiranyl groups of Formula II and the radical R in known manner into the isocyanuric acid ring is also claimed.

15 Claims, No Drawings

THERAPEUTIC COMPOSITIONS WITH A CYTOSTATIC ACTION CONTAINING ISOCYANURIC ACID DERIVATIVES AND PROCESS OF MANUFACTURE

BACKGROUND OF THE INVENTION

The present invention relates to novel isocyanurates having at least two oxiranyl groups and the use of the same to treat malignant neoplasias and therapeutic compositions with a cytostatic action containing said isocyanurates having at least two oxiranyl groups.

It is known that a number of alkylating substances develop a cytostatic or cytotoxic effect. The best known compounds are derived from the so-called nitrogen mustards. Beyond that it is also known to use compounds containing at least two epoxy groups in the molecule as cancerostatic agents. Such compounds are, for instance, 4,4'-bis-(2,3-epoxypropyl)-di-piperidinyl-(1,1') and 1,2-15,16-diepoxy-4,7,10,13-tetraoxohexadecane. However, these diepoxide compounds did not provide substantial improvement in cytostatic treatment and they are hardly used. They are utilized only occasionally for the treatment of brain tumors. The wider applicability of the above-mentioned compounds is also prevented by their limited solubility.

The subject matter of commonly assigned copending U.S. Patent Application Ser. No. 95,229, filed Nov. 19, 1979, now abandoned in favor of continuation Ser. No. 257,893, filed Apr. 27, 1981, relates to therapeutic compositions having a cytostatic action which contain as the pharmacologically active ingredient triglycidyl isocyanurate (TGI) and/or such TGI derivatives where the hydrogen atom attached to the carbon in the 2 position of one or more of the glycidyl groups is replaced by an alkyl having from 1 to 4 carbon atoms. Compounds of this kind are characterized by the three nitrogen atoms of the isocyanuric acid ring being substituted by glycidyl groups containing epoxy groups, which can also be substituted in the 2 position with an alkyl having from 1 to 4 carbon atoms.

The subject matter of commonly assigned copending U.S. Patent Application Ser. No. 194,908, filed Oct. 7, 1980, likewise relates to cytostatically active pharmaceutical preparations which contain as the pharmacologically active ingredient isocyanurates corresponding to the formula

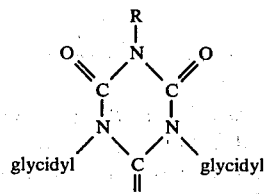

where R is alkyl, aryl, aralkyl, alkaryl, cycloalkyl, where these radicals may optionally be unsaturated with/or substituted and glycidyl represents a group of the formula

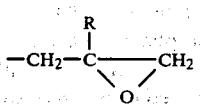

where R is hydrogen or an alkyl having from 1 to 4 carbon atoms.

OBJECTS OF THE INVENTION

An object of the present invention is the development of novel isocyanurates having two epoxy groups which have a cytostatic action.

Another object of the present invention is the development of N-substituted dioxiranyl isocyanurates having the formula

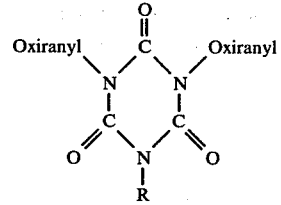

wherein each oxiranyl is the same or different and has the formula

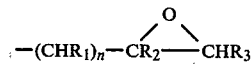

wherein $R_1$, $R_2$ and $R_3$ are the same or different and members selected from the group consisting of hydrogen, alkyl, haloalkyl, hydroxyalkyl and alkoxyalkyl and n is an integer from 1 to 8, with the proviso that if n is 1 in all oxiranyl groups, at least one of $R_1$ or $R_3$ is other than hydrogen, and R is a member selected from the group consisting of oxiranyl, as defined above, hydrogen, alkyl, alkenyl, hydrocarbon aryl, hydrocarbon aralkyl, hydrocarbon alkaryl, cycloalkyl and cycloalkenyl, optionally containing substituents.

A further object of the present invention is the development of a method for the preparation of the above N-substituted-dioxiranyl isocyanurates.

A still further object of the present invention is the obtaining of a therapeutic composition with a cytostatic action consisting essentially of a cytostatically effective amount—preferably being in the range of from 0.05% to 5% by weight—of at least one N-substituted-dioxiranyl isocyanurate having the formula

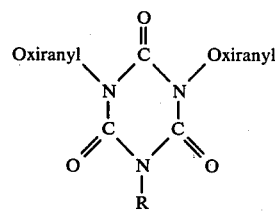

wherein each oxiranyl is the same or different and has the formula

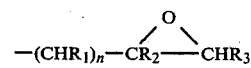

wherein $R_1$, $R_2$ and $R_3$ are the same or different and members selected from the group consisting of hydrogen, alkyl, haloalkyl, hydroxyalkyl and alkoxyalkyl and n is an integer from 1 to 8, with the proviso that if n is 1 in all oxiranyl groups, at least one of $R_1$ or $R_3$ is other than hydrogen, and R is a member selected from the group consisting of oxiranyl, as defined above, hydrogen, alkyl, alkenyl, hydrocarbon aryl, hydrocarbon aralkyl, hydrocarbon alkaryl, cycloalkyl and cycloalkenyl, optionally containing substituents, the remainder being conventional pharmaceutical vehicles.

A yet further object of the present invention is the development of a method for the treatment of malignant neoplasias in warm-blooded animals comprising administering a cytostatically effective amount of at least one N-substituted-dioxiranyl isocyanurate having the formula

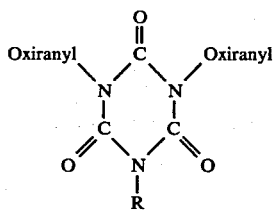

wherein each oxiranyl is the same or different and has the formula

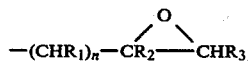

wherein $R_1$, $R_2$ and $R_3$ are the same or different and members selected from the group consisting of hydrogen, alkyl, haloalkyl, hydroxyalkyl and alkoxyalkyl and n is an integer from 1 to 8, with the proviso that if n is 1 in all oxiranyl groups, at least one of $R_1$ or $R_3$ is other than hydrogen, and R is a member selected from the group consisting of oxiranyl, as defined above, hydrogen, alkyl, alkenyl, hydrocarbon aryl, hydrocarbon aralkyl, hydrocarbon alkaryl, cycloalkyl and cycloalkenyl, optionally containing substituents, to a warm-blooded animal suffering from a malignant neoplasia.

These and other objects of the invention will become more apparent as the description thereof proceeds.

DESCRIPTION OF THE INVENTION

The present invention results from the observation that compounds which are structurally analogous to triglycidyl-isocyanurate, and N-substituted-diglycidyl-isocyanurate discussed above, also develop a surprisingly strong cytostatic effectiveness, which can even exceed that of TGI.

The structurally analogous compounds of the present invention contain on the isocyanuric acid ring either 2 or 3 N-substituted radicals containing epoxide groups, where at least one of these N-substituents differs in its structure from the glycidyl group of the above-mentioned previously filed applications.

The subjects of the present invention are therefore in a first embodiment medicinal preparations with cytostatic action, containing N-substituted-dioxiranyl-isocyanurate compounds of the general Formula I

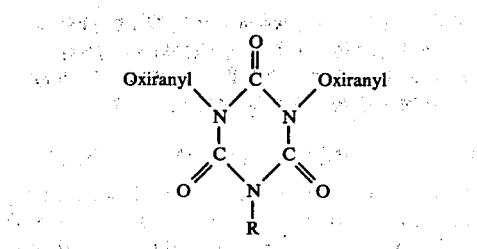

in which oxiranyl denotes identical or different radicals of the general Formula II

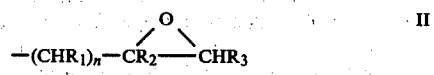

where $R_1$, $R_2$ and $R_3$ are identical or different, and denote hydrogen, alkyl, haloalkyl and/or alkoxyalkyl, and n denotes a number from 1 to 8, with the proviso that if n=1 in all the oxiranyl radicals, at least one of the radicals $R_1$ or $R_3$ is not hydrogen, and where furthermore R in the general Formula I denotes an oxiranyl radical of the general Formula II, hydrogen, or one of the following radicals: alkyl, aryl, aralkyl, alkaryl or cycloalkyl, which radicals can also be unsaturated and/or substituted, if desired.

More particularly, the present invention, in the above aspect, relates to a therapeutic composition with a cytostatic action consisting essentially of a cytostatically effective amount of at least one N-substituted-dioxiranyl isocyanurate having the formula

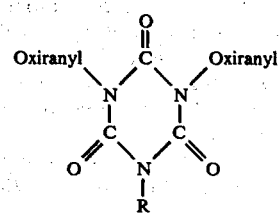

wherein each oxiranyl is the same or different and has the formula

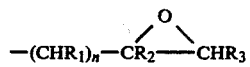

wherein $R_1$, $R_2$ and $R_3$ are the same or different and members selected from the group consisting of hydrogen, alkyl, haloalkyl, hydroxyalkyl and alkoxyalkyl and n is an integer from 1 to 8, with the proviso that if n is 1 in all oxiranyl groups, at least one of $R_1$ or $R_3$ is other than hydrogen, and R is a member selected from the group consisting of oxiranyl, as defined above, hydrogen, alkyl, alkenyl, hydrocarbon aryl, hydrocarbon aralkyl, hydrocarbon alkaryl, cycloalkyl and cycloalkenyl, optionally containing substituents, the remainder being conventional pharmaceutical vehicles.

In a second embodiment, the invention also relates to the novel N-substituted dioxiranyl isocyanurates having the formula

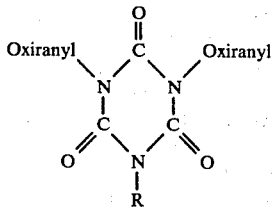

wherein each oxiranyl is the same or different and has the formula

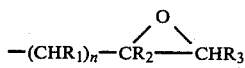

wherein $R_1$, $R_2$ and $R_3$ are the same or different and members selected from the group consisting of hydrogen, alkyl, haloalkyl, hydroxyalkyl and alkoxyalkyl and n is an integer from 1 to 8, with the proviso that if n is 1 in all oxiranyl groups, at least one of $R_1$ or $R_3$ is other than hydrogen, and R is a member selected from the group consisting of oxiranyl, as defined above, hydrogen, alkyl, alkenyl, hydrocarbon aryl, hydrocarbon aralkyl, hydrocarbon alkaryl, cycloalkyl and cycloalkenyl, optionally containing substituents.

In a third embodiment, the invention relates to processes for the production of the above N-substituted-dioxiranyl-isocyanurates.

In a fourth embodiment, the invention relates to a method for the treatment of malignant neoplasias in warm-blooded animals comprising administering a cytostatically effective amount of at least one N-substituted-dioxiranyl isocyanurate having the formula

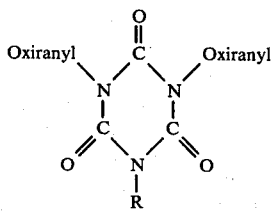

wherein each oxiranyl is the same or different and has the formula

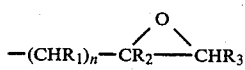

wherein $R_1$, $R_2$ and $R_3$ are the same or different and members selected from the group consisting of hydrogen, alkyl, haloalkyl, hydroxyalkyl and alkoxyalkyl and n is an integer from 1 to 8, with the proviso that if n is 1 in all oxiranyl groups, at least one of $R_1$ or $R_3$ is other than hydrogen, and R is a member selected from the group consisting of oxiranyl, as defined above, hydrogen, alkyl, alkenyl, hydrocarbon aryl, hydrocarbon aralkyl, hydrocarbon alkaryl, cycloalkyl and cycloalkenyl, optionally containing substituents, to a warm-blooded animal suffering from a malignant neoplasia.

In the compounds of the general Formula I, where R denotes a substituted radical from the group consisting of alkyl, hydrocarbon aryl, hydrocarbon aralkyl, hydrocarbon alkaryl, and cycloalkyl, which radicals can also be unsaturated, if desired, then the following radicals are present as substituents on this radical R: halogen, hydroxyl, amino, N-substituted amino, mercapto, alkylmercapto, arylmercapto, alkylsulfoxy, arylsulfoxy, alkoxy, aryloxy and/or acyloxy. One or several of the substituents mentioned here can be present in the radical R, and the substituents of the above-mentioned type can be identical or different. Preferred as unsaturated radicals are those with olefinically unsaturated bonds, particularly alkenyl and cycloalkenyl.

The N-substituted-dioxiranyl-isocyanurates according to the invention are characterized in that they contain in N-substitution on the isocyanuric acid ring at least 2 substituents with epoxide groups, where furthermore at least one of these radicals differ from the glycidyl radical III

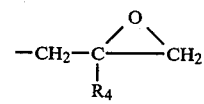

disclosed in the said patent application Ser. No. 257,893. In this formula $R_4$ is preferably hydrogen, but it can also denote alkyl with 1 to 4 carbon atoms. At least one of the oxiranyl radicals in N-substitution provided according to the present invention, has a constitution differing from the above-mentioned glycidyl radicals of Formula III within the framework of the definition for these radicals of the general Formula II according to the invention.

Taking into account these prerequisites, the following applies to the constitution of the oxiranyl radicals of the general Formula II. Preferably the substituents $R_1$, $R_2$ and/or $R_3$, when other than hydrogen are hydrocarbon skeletons, optionally substituted, and having from 1 to 10 carbon atoms. When $R_1$, $R_2$ and/or $R_3$ are alkyl or substituted alkyl, the corresponding radicals with 1 to 4 carbon atoms are preferred. It may be advisable to employ corresponding compounds with not more than 3 carbon atoms in these alkyls $R_1$ to $R_3$, particularly those compounds which have one or two carbon atoms in these alkyls. Because of their similarity to the highly effective TGI-derivatives of the said older patent application, compounds may be particularly preferred where these alkyls or substitute alkyls $R_1$ to $R_3$ have only one carbon atom, and here it may be preferred that not all, but only 2 or even only one of these radicals denote a corresponding alkyl radical or a substituted alkyl radical, while the remaining radicals are hydrogen. These data are of particular importance for the case where n denotes 1 in the oxiranyl radicals of the general Formula II. If n is a number different than 1, all radicals $R_1$ to $R_3$ can be hydrogen, in another preferred embodiment. If at least one of these radicals is in this case a substituted alkyl radical, the above-mentioned data regarding the preferred nature of these radicals again applies logically.

Preferred values for n are between 1 and 5, particularly 1 to 3. Compounds where n=2 or particularly n=1, are among the most important compounds in the sense of the invention; in the last-mentioned case, the above limitations have to be taken into consideration.

Among the preferred characteristics of the radicals $R_1$, $R_2$ and $R_3$ in the oxiranyl radicals of the general Formula II are the following:

$R_1$ is preferably hydrogen, an alkyl or a substituted alkyl with 1 to 3 carbon atoms. $R_2$ is preferably hydrogen or an alkyl or a substituted alkyl with 1 carbon atom, and $R_3$ is preferably hydrogen, an alkyl or a substituted alkyl with 1 to 2 carbon atoms. Generally speaking, compounds where $R_2$ is hydrogen can be particularly important, also compounds where $R_3$=hydrogen. Compounds of this type are characterized in that the epoxide group is unsubstituted in at least one or preferably in both carbon atoms of the epoxide ring.

The mechanism of action of the compounds used within the framework of the invention is not quite clear. But obviously it is the epoxide groups that are responsible for the cytostatic action, of which at least two are present in the compounds used according to the invention. Perhaps the importance of the third substituent—which may, but need not necessarily contain an epoxide group—lies in its influence on the distribution of the lipophilic and hydrophilic balance of the N-substituted-dioxiranyl isocyanurates, so that the absorption of the organism can be controlled to a certain extent. But the importance of this substituent R introduced according to the invention need not necessarily be limited to this function.

It was found, however, to be of advantage to subject the absolute size of the respective oxiranyl radicals in N-substitution to a certain limitation. Thus, the preferred oxiranyl radicals contain not more than 12, and preferably not more than 10 carbon atoms. It may be advisable to use radicals with up to 7, or even with only up to 4 or 5 carbon atoms. As mentioned above, 1 or 2 epoxide groups may be present in the sense of the general Formula III, provided at least one oxiranyl radical differing therefrom is present in the sense of the definition according to the invention.

The radical R in the compounds of the general Formula I used according to the invention can be a third oxiranyl radical in the sense of the definition according to the invention, hydrogen or a radical having a hydrocarbon skeleton, which can be substituted and/or contain hetero-atoms. This radical R contains not more than 12 carbon atoms, and preferably not more than 6 carbon atoms. Of interest can be radicals which contain up to 6 or preferably only up to 4 carbon atoms, these values being independent of the respective structure and referring to the sum of all carbon atoms in the respective radical.

Possible hetero-atoms in the substituent R are preferably N, O, S and/or P. The total number of hetero-atoms is preferably not more than 4. The hetero-atoms can be part of a substituent on the radical R, or they can be included directly in the hydrocarbon radical R.

In an especially preferred version of the invention, substituent R means an optionally substituted alkyl. This alkyl can be a straight chain or be branched or also alkenyl and contain, not counting substituents, preferably not more than 10, especially not more than 8, carbon atoms. In this version of the invention, there are especially preferred those compounds of general Formula I where the substituent R is a non-substituted alkyl with 1 to 6 carbon atoms or a corresponding alkyl which is substituted with halogen, hydroxyl, amino, N-substituted amino, mercapto, alkylmercapto, hydrocarbon arylmercapto, alkylsulfoxy, hydrocarbon arylsulfoxy, alkoxy, hydrocarbon aryloxy and/or acyloxy.

Such substituted substituents R can also be substituted once or repeatedly with the mentioned groups. Preferentially 1 to 3 of the mentioned substituents are located on the respective substituent R. In a particularly preferred case compounds of general Formula I, are used where R denotes a mono- or disubstituted alkyl radical of the said type, which is selected from the following group: monohydroxyalkyl, dihydroxyalkyl, halohydroxyalkyl, N-substituted aminohydroxyalkyl, acyloxyhydroxyalkyl, if necessary, substituted alkylmercaptohydroxyalkyl and alkoxyhydroxyalkyl. The alkyl radicals contain preferably 3 to 7, and particularly 3, 4 or 5 carbon atoms.

If substituting groups are present in the substituted alkyl radical R, which substitution groups in turn contain hydrocarbon radicals, particularly in the case of the radicals N-substituted amino, alkylmercapto, arylmercapto, alkoxy, aroxy and acyloxy, these substituted groups have preferably not more than 10, and particularly not more than 8 carbon atoms. The preferred limit is 6 carbon atoms, particularly not more than 4 carbon atoms. These substituting hydrocarbon radicals can in turn be aryl, aralkyl, alkaryl, cycloalkyl and/or alkyl radicals, which can also contain, if desired, substituents, like halogen, hydroxyl, etc.

Here also hetero-atoms containing substituents of the above-mentioned type can be present; thus, for example, heterocyclic ring systems with 1 to 3 heteroatoms of the above-mentioned type.

Within the framework of the invention can also be used compounds of the general Formula I where the radical R denotes a linear or branched unsubstituted alkyl with up to 6, preferably up to 4 carbon atoms. Particularly suitable are the radicals methyl, ethyl, propyl, isopropyl, and the corresponding $C_4$ radicals. Furthermore, those compounds of the general Formula I are particularly preferred where the radical R is a disubstituted alkyl with 3 or more carbon atoms and denotes preferably an alkyl substituted with at least one hydroxyl group. Most preferably a hydroxyl group is always next to another substituent in this disubstituted alkyl with 3 or more carbon atoms. Particularly important are those substituted compounds of Formula I which contain, in addition to the hydroxyl group, as other substituents, a second hydroxyl group, halogen, an N-substituted amino, an aklylmercapto, or an acyloxy. Chlorine and/or bromine are preferred as halogens; however, fluorine and iodine are not excluded. The N-substituted amino remnants can correspond to the formula:

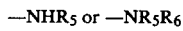

$$-NHR_5 \text{ or } -NR_5R_6 \qquad (III)$$

Here $R_5$ and $R_6$ radicals, respectively, are hydrocarbon radicals, which in turn can be substituted. In the preferred version of the invention, $R_5$ and, where present, $R_6$ contains up to 12 carbon atoms, where the carbon atoms of the disubstitution at the nitrogen of $R_5$ and $R_6$ is not to exceed the sum of 12 carbon atoms. The substituents $R_5$ and $R_6$ contain preferentially a total of up to 8 and particularly not more than 5 carbon atoms. The substituents $R_5$ and $R_6$ can also be joined into a saturated or unsaturated, possibly aromatic and/or heterocyclic ring, which heterocyclic ring can also contain other hetero-atoms, particularly N, O and/or S with preferably 5 or 6 ring members. If these radicals are in turn substituted again, particularly hydroxyl or halogen, preferably chlorine or bromine are provided according to the invention as such substituents.

If an acyloxy radical is present in R, in addition to the hydroxyl group, this acyloxy radical contains preferably likewise up to a maximum of 10 carbon atoms, the preferred limit being here again 8 carbon atoms, and it is particularly preferred not to introduce more than 5 carbon atoms into the molecule at this point. Preferred are here, too, alkanoyloxy radicals with the corresponding number of carbon atoms, though aroyloxy radicals are not excluded. The acyloxy radicals derive preferably from monocarboxylic acids with the said number of carbon atoms and structure. The same data also apply analogously to alkoxy-, alkylmercapto- or arylmercapto substituents on R.

In a particularly important embodiment of the invention, the radical R contains two hydroxyl groups on a linear branched alkyl radical of the above-mentioned type. Such radicals can be created by opening the epoxide group of an oxiranyl radical with water. Compounds of this type are formed, for example, in this way, that a compound of the general Formula I substituted with 3 oxiranyl radicals is reacted with water in a molar ratio of 1:1.

If R is an aryl, aralkyl or alkaryl substituent, where aryl represents a hydrocarbon aryl, then particularly single ring substituents are preferred. Phenyl, benzyl, tolyl, xylyl and related compounds are typical representatives. Also where the substituent R is cycloaliphatic, single ring systems on the basis of cyclopentyl, cyclohexyl and their derivatives are preferred. Correspondingly, of the heterocyclic substituents, thus especially single ring cyclic compounds with O, N and/or S in the system fall within the frame of the invention. These ring systems can thus preferentially contain 1, 2 or 3 such hetero-atoms. These heterocyclic substituents contain preferentially 5 or 6 ring elements. If desired, all ring substituents mentioned above, be they of aromatic or cycloaliphatic nature, can themselves contain further substituents. Suitable substituents are, for instance, halogen or alkoxy.

The medicinal preparations according to the invention can contain preferably individual, defined compounds of general Formula I. However, it has been shown that ingredient mixtures of several compounds under the general Formula I are highly effective cytostatica. The medicinal preparations preferably contain from 0.05% to 5% by weight of at least one compound of the general Formula I, and the remainder to 100% conventional inert aqueous pharmaceutical vehicles.

The preparation of active ingredients of Formula I is a further objective of the invention. Basically the reaction mechanisms are known and the following possibilities of reaction exist without any claim to completeness.

(1) Triepoxy compounds of the general Formula I can be prepared particularly by reacting the cyanuric acid or its salts with the corresponding alkenyl halides and subsequent epoxidation of the alkenyl group. See U.S. Pat. No. 3,376,301 and Houben-Weyl, Methoden der organischen Chemie, vol. 6/3, 385 ff.

A synthesis reaction of cyanuric acid with α-halogenepoxides and subsequent separation of hydrogen halide is also possible, see DOS No. 19 54 531 and Angew.-Chem. 80 (1968) 851.

(2) The preparation of diepoxide compounds of the general Formula I can follow the following procedure. Their production can also be effected in known manner. Preferably employed is the reaction of triepoxyisocyanurate compounds with a deficit of water, alcohol, primary and/or secondary amines, mercaptans, imines, imides, carboxylic acids, hydrogen halide, etc. or hydrogen.

Due to the equivalence of the three epoxy groups, this reaction leads initially always to product mixtures, which by themselves can be therapeutically effective. But it is also possible, and part of the following described procedure of the invention, to separate out from these mixtures the corresponding compounds of general Formula I, through suitable separating procedures, for instance, through preparative thin-layer chromatography or column chromatography.

Within the scope of this reaction, one epoxy group is converted into the substituent R of the compounds of the general Formula I.

During the reduction treatment of the oxiranyl group with hydrogen or with hydrogen-producing compounds, a monohydroxyalkyl substituent R is produced. The hydrogen-producing compounds which can be used are, for instance, hydride compounds, such as complex boron hydrides, for example, sodium borohydride. In the other cases mentioned, the original trioxiranyl compound is reacted with a deficit of a nucleophilic compound $H^{\oplus} A^{\ominus}$, whereby a disubstituted substituent R is produced which contains, apart from a hydroxyl group, the substituent $A^{\ominus}$ as a second substituent, normally at the adjacent carbon atom to the hydroxylated carbon atom of the radical R. Basically, the reaction of oxiranyl groups with such nucleophilic reaction partners is a known state of technology and has, for instance, been described in Angew. Chemie 80, 851 (1968). However, within the current technology this reaction is made deliberately on more than one epoxide group and serves, for instance, in an industrial situation to establish crosslinking in epoxide resin systems. In the method according to this invention, procedural conditions are preferentially selected which enable a far-reaching increase in the yield, in the direction of 1:1 of the reaction products, as well as the subsequent isolation and extraction of these 1:1 reaction products, with the separation of unreacted constituents of the original material and other reaction products which are obtained by the reaction of more than one epoxide group with the nucleophilic reaction partner.

In the reaction of epoxy compounds with nucleophilic reaction partners $H^{\oplus} A^{\ominus}$ of the above-mentioned type, it can be difficult to obtain the desired 1:1 reaction products in the preferred yield, since the three epoxide groups of the molecule of the original compound are about identical in the reaction, and thus the desired dioxiranyl compound is frequently not formed as the preferred reaction product. The attempt to enrich the desired compound by reacting the trioxiranyl isocyanurate with a deficiency of the nucleophilic reaction partner is only feasible in few cases, because there occurs in many cases an onset of polymerization of the oxiranyl isocyanurate.

The extraction of the 1:1 reaction products succeeds relatively easy, as a rule, only when mercaptans, amines and hydrides are selected as reactants. Hereby one can obtain partial epoxide ring opening products of the desired constitution, with starting mixtures which contain the reactants in a ratio of 1:1 or with only a slight excess of one of the reactants. More difficult is the obtaining of the corresponding reaction products when, for instance, carboxylic acids, water or alcohols are employed.

It was found that the preparation of the 1:1 reaction product becomes surprisingly simple when one reacts trioxiranyl isocyanurate with an excess, and preferably with a large excess, of the nucleophilic reactant $H^{\oplus}$ A⊖, terminates the reaction prematurely and then separates the excess of nucleophilic reaction partner, the unreacted isocyanurate and the also formed di- and tri-addition products. The remaining raw dioxiranyl product can then in a conventional manner, for instance through column chromatography, be purified. In this process the nucleophilic reaction partner is used in a 3 to 30 fold excess, especially in a 5 to 20 fold excess of the required amount, 1:1 molar ratio. The reaction can be conducted in solvents and, if possible, the excess of nucleophilic reaction partner can serve as a solvent. If solvents are being used, these should be suitably polar but not reactive under the selected operating conditions. Preferably the solvent is not water miscible. Through the selection of a proper solvent, the polymerizing tendency of the trioxiranyl isocyanurate is suppressed and side reactions, through the addition of solvent to the epoxide group, is avoided. In addition, the working up of the reaction mixture through the separation of the reactants and the undesired reaction products can be facilitated by proper solvent selection. Especially suitable solvents are, for example, halogenated hydrocarbons, particularly chlorinated hydrocarbons. The reaction is commonly conducted at temperatures between about 30° C. and 100° C., preferably 40° C. to 100° C. The reaction temperature is selected in a particularly suited version, so that within four to five hours the epoxide content of the reaction mixture has been reduced by one half.

By the selection of proper reaction parameters, the purification of the reaction raw product is frequently possible in a very simple manner. The excess of the nucleophilic reaction partner, part of the oxiranyl compound, as well as the component of the reaction product wherein all three epoxide groups are reacted, can frequently be removed by extraction of the organic phase with water. The solvent is evaporated from the residual reaction mixture. On taking up the residual reaction mixture in methanol, the unreacted trioxiranyl isocyanurate remains undissolved and can be separated. Finally, after evaporation of the methanol, only the raw dioxiranyl compound (1:1 reaction product) remains, which can be purified through simple fractionation, for instance, column chromatography. The eluant may, for example, be methylene chloride/ethyl acetate or methylene chloride/acetone. Purification and extraction of the 1:1 reaction product containing two epoxide groups from the mixture of reactants is, here and in the other methods described below, as a rule, an essential step in the process as per the invention. For the manufacture of sulfoxy compounds from the corresponding mercapto compounds, see Houben-Weyl cited above, Vol. 9, 207–217 (1955), as well as Makromol. Chem. 169, 323 (1979).

(3) A very elegant general method for the preparation of compounds from general Formula I is based on the reaction of mono-N-substituted isocyanuric acid with epihalohydrins. The preparation of mono-N-substituted isocyanuric acids can be made with known published methods. For the relevant literature one is, for instance, referred to W. J. Close, J. Am. Chem. Soc. 75, 3617 (1953). This source describes apart from older relevant works, a generally applicable process where mono-substituted biuret compounds are reacted with alkyl carbonates, especially ethyl carbonate, in the presence of an alkali metal alkoxide, especially sodium ethoxide, to produce a mono-N-substituted isocyanuric acid. The substitute introduced by this process corresponds, as a rule, to substitutent R in compounds of general Formula I.

In a follow-up reaction the two oxiranyl groups are then introduced. For this purpose, the mono-N-substituted isocyanuric acid is reacted with the required epihalohydrin compound, for instance, with epichlorohydrin. This reaction also takes place in the known manner. It can be made in the presence of a small amount of a quarternary ammonium compound as catalyst. (For this, see for instance, Houben-Weyl, Methoden der organischen Chemie, Vol. 14/2, 497, 547 [1963].)

In a modification of this reaction mechanism, the mono-N-substituted isocyanuric acid is not directly reacted with the epoxide compound. Instead, initially it is reacted with an allyl halide or other alkenyl halide which corresponds to the oxiranyl radical of the compounds belonging to general Formula I. However, instead of the epoxide group, they have an olefinic double bond. The then prepared alkenyl substituted isocyanurates are then epoxidized on the double bond. The epoxidation is accomplished according to established procedures with peracids. For instance, the reaction of cyanuric acid with an allyl halide is described in U.S. Pat. No. 3,376,301. The epoxidation of allyl isocyanurates with peracids is, for instance, described in Houben-Weyl, see above, Vol. 6/3, 385 ff.

The reaction can be conducted in polar aprotic solvents, which dissolve one reaction partner at least partially and which are inert to the reactants. A particularly useful solvent medium is the class of dialkylformamides, especially the lower dialkylformamides, such as dimethylformamide. The mono-N-substituted isocyanuric acid compound can be utilized as such or as a salt. The preferred reaction time is one to ten hours, particularly two to five hours.

The epoxidation of the allyl groups by means of peracids is also preferably conducted in the presence of solvents. Suitable are polar solvents, such as, for example, halogenated carbons or alcohols. The suitable reaction temperature is customarily in the range from 0° to 50° C., especially between 10° C. to 30° C. The peracid is utilized ideally in an approximately equivalent amount or in only slight excess. m-chloro-perbenzoic acid is easily accessible as a commercial product and it is suited for accomplishing the reaction. The reaction time is, as a rule, in the area of 24 hours or more, for instance, up to 48 hours.

A further object of the present invention is the development of a process for the preparation of N-substituted-dioxiranyl-isocyanurates of general Formula I:

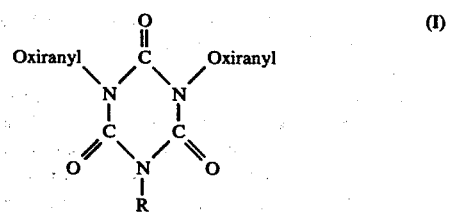

(I)

wherein each oxiranyl is the same or different and has the formula

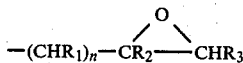

wherein $R_1$, $R_2$ and $R_3$ are the same or different and members selected from the group consisting of hydrogen, alkyl, haloalkyl, hydroxyalkyl and alkoxyalkyl and n is an integer from 1 to 8, with the proviso that if n is 1 in all oxiranyl groups, at least one of $R_1$ or $R_3$ is other than hydrogen, and R is a member selected from the group consisting of oxiranyl, as defined above, hydrogen, alkyl, alkenyl, hydrocarbon aryl, hydrocarbon aralkyl, hydrocarbon alkaryl, cycloalkyl and cycloalkenyl, optionally containing substituents. This process is characterized in that:

(A) the two oxiranyl groups are introduced into the mono-N-substituted isocyanuric acid substituted with substituent R to give a product of general Formula I, or (B) a trioxiranyl isocyanurate with oxiranyl remnants of general Formula II is subjected to a partial reaction with water, alcohols, compounds with a primary or secondary amino group, mercaptans, hydrogen sulfide, carboxylic acids, hydrohalic acids or hydrogen or compounds giving off hydrogen, optionally the thus-formed mercapto compounds are converted to the respective sulfoxy compounds, and the formed reaction products of general Formula I are recovered from the reaction mixture.

If in this procedure the two oxiranyl groups of general Formula II are introduced into mono-N-substituted isocyanuric acid, this can be accomplished in such a manner by either reacting mono-N-substituted isocyanuric acid containing substituent R with an epihalohydrin, whereby the epihalohydrin compound corresponds to the oxiranyl group of Formula II, or initially reacting the mono-N-substituted isocyanuric acid with the corresponding alkenyl halide, followed by epoxidation, preferably with peracids, of the alkenyl group or with the substituted alkenyl group, respectively, to convert the same to the oxiranyl group.

Typical examples of compounds of the general Formula I are the following:

1. Di-2,3-epoxybutyl-but-2-enyl isocyanurate
   ($R = -CH_2-CH=CH-CH_3$, $R_1$, $R_2=H$, $R_3=-CH_3$, n=1).
   Colorless, viscous liquid. P0 2. Tri-2,3-epoxybutyl isocyanurate

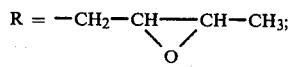

R, $R_2=H$, $R_3=-CH_3$, n=1)
Colorless, viscous liquid.

3. Tri-3,4-epoxybutyl-isocyanurate

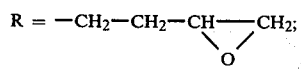

$R_1$, $R_2$, $R_3=H$, n=2)
Colorless, viscous liquid, crystallized slowly after standing for several days.

4. Tri-4,5-epoxypentyl isocyanurate

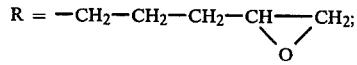

$R_1$, $R_2$, $R_3=H$, n=3)
Colorless, viscous liquid.

5. Tri-5,6-epoxyhexyl isocyanurate

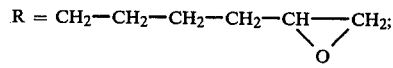

$R_1$, $R_2$, $R_3=H$, n=4)
Colorless, viscous liquid.

Other compounds which fall within the framework of the present invention are, for example, Di-2,3-epoxybutyl-methyl isocyanurate, di-2,3-epoxybutylbutyl isocyanurate, di-3,4-epoxybutyl-but-3-enyl isocyanurate, di-4,5-epoxypentyl-pent-4-enyl isocyanurate, di-5,6-epoxyhexyl-hex-5-enyl isocyanurate, di-4,5-epoxypentylpentyl isocyanurate, di-5,6-epoxyhexyl-hexyl isocyanurate, di-3,4-epoxybutyl-butyl isocyanurate, tri-(1-methyl-2,3-epoxy)propyl isocyanurate, di-(1-methyl-2,3-epoxy)-propyl(1-methyl-prop-2-enyl)isocyanurate, tri-2,3-epoxypentyl isocyanurate, tri-3,4-epoxypentyl isocyanurate, tri-2,3-epoxyhexyl isocyanurate, tri-3,4-epoxyhexyl isocyanurate, tri-4,5-epoxyhexyl isocyanurate, tri-(2-methyl-2,3-epoxy)butyl isocyanurate, tri(4-methyl-4,5-epoxy)-pentyl isocyanurate, tri-(4-methyl-4,5-epoxy)-hexyl isocyanurate, tri(3-phenyl-2,3-epoxy)-propyl isocyanurate, tri-(3-methoxycarbonyl-2,3-epoxy)-propyl isocyanurate, tri-1,2-epoxycyclohexylmethyl isocyanurate, tri-7,8-epoxyoctyl isocyanurate.

Very generally, in the scope of the invention, it is preferable that the compounds of general Formula I with substituent R, that are employed, are those where the substituent R, at least under normal conditions, should display no substantial reactivity, or none at all with the epoxide group of the oxiranyl substituent or substituents on the ring system of general Formula I. This assures that the active ingredients used as per the invention have a sufficiently long storage life and that undesirable reactions, causing destruction of the epoxide group do not occur. This prerequisite has to be kept in mind, especially also for the selection of possibly substituents R.

The compounds of the general Formula I used according to the invention appear in various stereo-isometric forms. Principally all these different forms are suitable for the purposes of the invention. They can be used in mixture or in the form of certain isolated isomers.

For utilization as cancerostatica the active ingredients should be applied by means of suitable vehicles. For that purpose the common pharmaceutical excipients for pharmacological preparations are suitable.

In animal experiments the utilization of freshly prepared, aqueous solutions, which were given i.p. or i.v., has proven to be useful. Compounds used as per the invention are effective against various forms of leukemia, including a reduction in the number of P388 tumor type cells in mice as well as neoplasms, such as lung carcinoma, colon carcinoma, melanoma, ependymoblastoma and sarcoma.

A combination therapy in connection with other cytostatica is possible.

The following Examples are illustrative of the practice of the invention without being limitative thereof. In the Examples, the percentage figures given are percent by weight unless otherwise designated.

EXAMPLE 1

Preparation of tri-2,3-epoxybutyl isocyanurate (compound 2)

29.6 gm (0.152 mol) of trisodium cyanurate and 42.1 gm (0.456 mol) of 1-chlorobutene-2 were stirred in 70 ml of dimethyl formamide for 3.5 hours at 120° C. After cooling to 100° C., 100 ml of toluene were added and the mixture was treated with 10% common salt solution. The organic phase was separated, and the solvent distilled off. 42.3 gm of a viscous liquid remained. Crystallization in methanol yielded 24 gm of colorless crystals, having a melting point of 77° C. This corresponds to a 53% yield of tri-but-2-enyl isocyanurate.

5 gm (0.017 mol) of tri-but-2-enyl isocyanurate were dissolved in 15 ml of methylene chloride, mixed with 10.9 gm of 90% m-chloroperbenzoic acid (0.057 mol) and stirred for 2.5 hours at room temperature, and then left standing over night. The oxidation is slightly exothermic. After the reaction was completed, the product was filtered from the precipitated m-chlorobenzoic acid. Any remaining per acid was destroyed by shaking with bisulfite solution, and the acid was extracted with aqueous hydrogen carbonate solution. After the solvent was distilled off, 10.3 gm of a liquid product mixture remained, which was separated by column-chromatography with silica gel G (Merck) and methylene chloride/acetone 95/5 as eluant. 7.8 gm (68%) of tri-2,3-epoxybutyl isocyanurate was obtained as a viscous, colorless liquid with 14.0% epoxide oxygen.

EXAMPLE 2

Preparation of tri-3,4-epoxybutyl-isocyanurate (compound 3)

9.8 gm (0.05 mol) of trisodium cyanurate and 20.4 gm (0.15 mol) of 1-bromobutene-3 were stirred into 20 ml of dimethyl formamide for 6 hours at 120° C. After the working up, as described in Example 1, the product was filtered through silica gel. After the solvent was removed, 6.8 gm of a liquid were obtained, which was homogeneous according to the thin-layer chromatography.

Iodine number: 257. 6.8 gm (46%) yield of tri-but-3-enyl isocyanurate.

6.8 gm (0.023 mol) of tri-but-3-enyl isocyanurate and 22.2 gm (0.116 mol) of m-chlorperbenzoic acid were stirred into 300 ml methylene chloride for 7 hours at 25° to 30° C. and left standing over night at room temperature. After reduction of the excess per acid, extraction of the acid, and distillation of the solvent as described in Example 1, 3.5 gm of a viscous liquid with 13.4% epoxide oxygen remained. The product contained 95% tri-3,4-epoxy-butyl isocyanurate.

Testing of the compounds of Example 1 and Example 2 according to the test specification of the National Cancer Institute, Bethesda, Md. 20014, published in "Cancer Chemotherapy Report", part 3, Sept. 1972, Vol. 3, No. 2, showed a significant extension of the mean survival time of the treated animal group with tumor p. 388 (leukemia) compared to an untreated animal group.

The above procedures are illustrative of the procedures employed in the production of compounds 4 and 5. Compound 1 was produced by partial epoxidation of tri-but-2-enyl isocyanurate.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. N-substituted dioxiranyl isocyanurates selected from the group consisting of:
   di-2,3-epoxybutyl-but-2-enyl isocyanurate,
   tri-2,3-epoxybutyl isocyanurate,
   tri-3,4-epoxybutyl isocyanurate,
   tri-4,5-epoxypentyl isocyanurate,
   tri-5,6-epoxyhexyl isocyanurate,
   di-2,3-epoxybutyl-methyl isocyanurate,
   di-2,3-epoxybutyl-butyl isocyanurate,
   di-3,4-epoxybutyl-but-3-enyl isocyanurate,
   di-4,5-epoxypentyl-pent-4-enyl isocyanurate,
   di-5,6-epoxyhexyl-hex-5-enyl isocyanurate,
   di-4,5-epoxypentyl-pentyl isocyanurate,
   di-5,6-epoxyhexyl-hexyl isocyanurate,
   di-3,4-epoxybutyl-butyl isocyanurate,
   tri-(1-methyl-2,3-epoxy)propyl isocyanurate,
   di-(1-methyl-2,3-epoxy)-propyl-(1-methyl-prop-2-enyl) isocyanurate,
   tri-2,3-epoxypentyl isocyanurate,
   tri-3,4-epoxypentyl isocyanurate,
   tri-2,3-epoxyhexyl isocyanurate,
   tri-3,4-epoxyhexyl isocyanurate,
   tri-4,5-epoxyhexyl isocyanurate,
   tri-(2-methyl-2,3-epoxy)-butyl isocyanurate,
   tri-(4-methyl-4,5-epoxy)-pentyl isocyanurate,
   tri-(4-methyl-4,5-epoxy)-hexyl isocyanurate,
   tri-(3-phenyl-2,3-epoxy)-propyl isocyanurate,
   tri-(3-methoxy-carbonyl-2,3-epoxy)-propyl isocyanurate,
   tri-1,2-epoxy-cyclohexylmethyl isocyanurate, and
   tri-7,8-epoxyoctyl isocyanurate.

2. A cytostatic composition consisting essentially of a cytostatically effective amount of at least one N-substituted-dioxiranyl isocyanurate having the formula

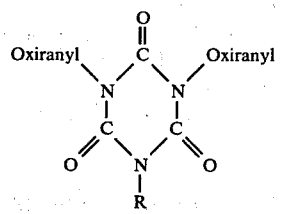

wherein each oxiranyl is the same or different, has not more than 12 carbon atoms and has the formula

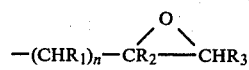

wherein $R_1$, $R_2$ and $R_3$ are the same or different and members selected from the group consisting of hydrogen, alkyl, haloalkyl, hydroxyalkyl and alkoxyalkyl and n is an integer from 1 to 8, with the proviso that if n is 1 in all oxiranyl groups, at least one of $R_1$ or $R_3$ is other than hydrogen, and R has not more than 12 carbon atoms and is a member selected from the group consisting of oxiranyl, as defined above, hydrogen, alkyl, alkenyl, hydrocarbon aryl, hydrocarbon aralkyl, hydrocarbon alkaryl, cycloalkyl and cycloalkenyl, which R may have further substituents selected from the group consisting of hydroxy, halogen, amino, mercapto, alkylmercapto, hydrocarbon arylmercapto, alkylsulfoxy, hydrocarbon arylsulfoxy, alkoxy, hydrocarbon aryloxy, and alkanoyloxy, and a pharmaceutically acceptable carrier therefor.

3. The cytostatic composition of claim 2 wherein at least one of $R_1$, $R_2$ and $R_3$ of said oxiranyl is selected from the group consisting of alkyl having from 1 to 4 carbon atoms, haloalkyl having from 1 to 4 carbon atoms, hydroxyalkyl having from 1 to 4 carbon atoms and alkoxyalkyl having from 3 to 4 carbon atoms.

4. The cytostatic composition of claim 2 or 3 wherein the total number of carbon atoms in said oxiranyl is not more than 10.

5. The cytostatic composition of claim 4 wherein the total number of carbon atoms in said oxiranyl is not more than 8.

6. The cytostatic composition of claim 2 or 3 wherein n is an integer from 1 to 5.

7. The cytostatic composition of claim 6 wherein n is an integer from 1 to 3.

8. The cytostatic composition of claim 4 wherein n is an integer from 1 to 5.

9. The cytostatic composition of claim 8 wherein n is an integer from 1 to 3.

10. The cytostatic composition of claim 2 or 3 wherein at least one of $R_1$ of said oxiranyl is selected from the group consisting of hydrogen, alkyl having from 1 to 3 carbon atoms, haloalkyl having from 1 to 3 carbon atoms, hydroxyalkyl having from 1 to 3 carbon atoms and methoxyethyl.

11. The cytostatic composition of claim 2 or 3 wherein at least one of $R_2$ of said oxiranyl is selected from the group consisting of hydrogen, methyl, halomethyl and hydroxymethyl.

12. The cytostatic composition of claim 2 or 3 wherein at least one of $R_3$ of said oxiranyl is selected from the group consisting of hydrogen, methyl, ethyl, halomethyl, haloethyl, hydroxymethyl and hydroxyethyl.

13. The cytostatic composition of claim 2 or 3 wherein R has from 1 to 10 carbon atoms.

14. The cytostatic composition of claim 2 or 3 wherein R has from 1 to 6 carbon atoms.

15. A cytostatic method in warm-blooded animals comprising administering a cytostatically effective amount of at least one N-substituted-dioxiranyl isocyanurate having the formula

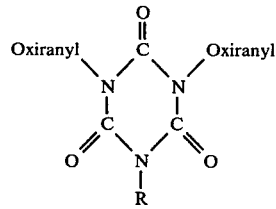

wherein each oxiranyl is the same or different, has not more than 12 carbon atoms and has the formula

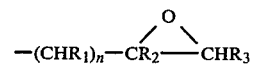

wherein $R_1$, $R_2$ and $R_3$ are the same or different and members selected from the group consisting of hydrogen, alkyl, haloalkyl, hydroxyalkyl and alkoxyalkyl and n is an integer from 1 to 8, with the proviso that if n is 1 in all oxiranyl groups, at least one of $R_1$ or $R_3$ is other than hydrogen, and R has not more than 12 carbon atoms and is a member selected from the group consisting of oxiranyl, as defined above, hydrogen, alkyl, alkenyl, hydrocarbon aryl, hydrocarbon aralkyl, hydrocarbon alkaryl, cycloalkyl and cycloalkenyl, which R may have further substituents selected from the group consisting of hydroxy, halogen, amino, mercapto, alkylmercapto, hydrocarbon arylmercapto, alkylsulfoxy, hydrocarbon arylsulfoxy, alkoxy, hydrocarbon aryloxy, and alkanoyloxy, to a warm blooded animal.

* * * * *